United States Patent [19]
Berger et al.

[11] Patent Number: 4,777,960
[45] Date of Patent: Oct. 18, 1988

[54] METHOD AND APPARATUS FOR THE ASSESSMENT OF AUTONOMIC RESPONSE BY BROAD-BAND EXCITATION

[75] Inventors: Ronald D. Berger, Brookline; Jerome P. Saul, Jamaica Plain; Ming H. Chen, Boston; Richard J. Cohen, Newton Highlands, all of Mass.

[73] Assignee: Massachusetts Institute of Technology, Cambridge, Mass.

[21] Appl. No.: 897,603

[22] Filed: Aug. 18, 1986

[51] Int. Cl.⁴ .................................................. A61B 5/05
[52] U.S. Cl. ...................................... 128/706; 128/670; 128/671; 128/741; 128/732; 364/413.03; 364/413.06
[58] Field of Search ............... 128/670, 671, 706, 741, 128/732; 364/415, 417

[56] References Cited
U.S. PATENT DOCUMENTS

| | | |
|---|---|---|
| 4,166,452 | 9/1979 | Generales, Jr. .................. 128/741 |
| 4,305,402 | 12/1981 | Katims ............................... 128/741 |
| 4,493,327 | 1/1985 | Bergelson et al. ................ 364/417 |
| 4,519,395 | 5/1985 | Hrushesky .......................... 128/671 |
| 4,616,659 | 10/1986 | Prezas et al. ....................... 128/706 |
| 4,649,482 | 3/1987 | Raviv et al. ........................ 364/417 |

*Primary Examiner*—William E. Kamm
*Assistant Examiner*—Timothy J. Keegan

[57] ABSTRACT

A rapid, noninvasive technique for quantifying the dynamic response of the autonomic nervous system (ANS) to perturbations it senses over a broad range of physiologically relevant frequencies. The technique involves two steps. First, a physiologic parameter sensed by the ANS is subjected to a broad-band perturbation as an input signal while a physiologic parameter modulated by the ANS is monitored as an output signal. Then, the transfer relation between input signal and output signal is determined. The computed transfer relation is then readily interpretable in terms of responsiveness of the various limbs of the ANS.

33 Claims, 3 Drawing Sheets

METHOD AND APPARATUS FOR THE ASSESSMENT OF AUTONOMIC RESPONSE BY BROAD-BAND EXCITATION

BACKGROUND OF THE INVENTION

The Government has rights in this invention pursuant to Grant No. NAG2-327 awarded by the National Aeronautics and Space Administration.

The role of the cardiorespiratory system is to maintain perfusion of appropriately oxygenated blood to the various tissues and organs of the body. This operation is carefully regulated by the ANS, which continuously senses hemodynamic variables that reflect the adequacy of tissue perfusion, such as arterial blood pressure and oxygen content, and then effects changes in respiration, cardiac output, and vascular resistance so as to maintain these variables within a narrow range. In this regard the ANS, combined with the effector organs it regulates, serves as a feedback and control system. It is well known that the performance of this feedback system becomes compromised in a variety of pathological conditions, such as heart failure, hypertension, shock, and diabetes, to name but a few. Quantitative assessment of the performance of the ANS would therefore be a vital tool in a wide range of clinical situations. Until now, however, there has existed no reliable noninvasive technique for achieving this quantitative assessment of autonomic function.

Performance of a feedback system can be ascertained by measuring the degree to which it can effect the appropriate changes in the variables it controls in response to fluctuations in the variables it senses. Thorough evaluation of the system's performance requires testing its response to a set of perturbations that fully represents the range of natural perturbations the system experiences. Most of the previously described techniques developed to characterize the ANS involve either not perturbing the system at all and measuring spontaneous fluctuations in hemodynamic variables [1,2,4,5,6,7,9,10,14,16,19,25], or measuring the system's response to perturbations applied at only a single frequency at a time [3,8,11,12,13,17,20,21,22,23]. The numbers in brackets refer to references listed in Appendix A. In the first case, the investigator's ability to examine system behavior is limited to the generally narrow frequency bands within which spontaneous fluctuations perturb the system. Furthermore, as these spontaneous perturbations are often in the form of an unmeasurable noise component, one is left with the task of attempting to infer information about the system from measurements of its output signals only. In the second case, since information about the system can be acquired at only one frequency at a time, a complete characterization using this sort of approach necessitates repeating the test procedure at many different frequencies. Such a protocol is cumbersome, as it requires a long time to complete. In addition, any system characterization derived from data pooled from multiple test trials may possess artifacts related to changes in test conditions from one trial to another.

A technique that would allow for rapid simultaneous acquisition of all information required to fully characterize the dynamic behavior of the ANS would therefore represent a tremendous improvement in the practical utility of this clinical tool. The approach we have developed requires a single typically six-minute period of data collection from which the system characterization over all frequencies of interest is derived.

In order to obtain a characterization of system responsiveness over the entire range of physiologically important frequencies (generally considered 0.0–0.5 Hz) from a single six-minute record of input and output signals, the input, or perturbing, signal must simultaneously contain components at all frequencies within this range. The input signal must therefore be of a "broad-band" or "white noise" nature.

The use of a broad-band excitation in exploring the mechanical properties of the cardiovascular system was described by Taylor [24]. He applied randomly timed pacing impulses to the cardiac atria of experimental animals via surgically implanted pacing wires, and characterized the transmission line properties of the arterial tree through the computation of an impedance function in the frequency domain. He found that the effective impedance of the arterial system was depressed at frequencies less than 0.03 Hz. Taylor pointed out that this behavior indirectly demonstrates the presence of compensatory mechanisms within the ANS that modulate arterial resistance at low frequencies. He made no attempt, however, to explicitly characterize the dynamic response of the ANS in performing this function. In contrast, the technique we present here provides a means for probing the specific transfer properties of the ANS, entirely noninvasively. Furthermore, we have found that our technique is surprisingly sensitive in its ability to quantify subtle changes in the performance of this feedback system.

SUMMARY OF THE INVENTION

The present invention assesses response of the autonomic nervous system by subjecting the autonomic nervous system to a broad-band perturbation. A hemodynamic parameter modulated by the autonomic nervous system, such as heart rate, is monitored and the transfer relation of the broad-band perturbation and the hemodynamic parameter is computed. A suitable perturbation of the autonomic nervous system is a broad-band perturbation on respiratory activity as measured by instantaneous lung volume. Other suitable perturbations of the autonomic nervous system will be described hereinbelow.

BRIEF DESCRIPTION OF THE DRAWING

The invention disclosed herein will be understood better with reference to the drawing in which.

DESCRIPTION OF THE PREFERRED EMBODIMENTS

Our technique requires first identifying appropriate hemodynamic or respiratory variables to represent input and output signals for the ANS. An appropriate input signal is one that reflects cardiorespiratory activity sensed by the ANS, and is controllable to allow imposition of a desired waveform on it. The output signal must be easily and noninvasively measurable and should reflect hemodynamic changes effected by the ANS.

While the ANS performs its function through modulation of multiple hemodynamic variables, heart rate is a particularly useful metric of autonomic function. This is because in the absence of autonomic control (e.g., after ablation of the neural networks through which the ANS communicates with its effector organs), the heart rate remains virtually constant. Heart rate is thus a relatively pure reflection of autonomic activity, and for this reason serves as the exemplary output variable in the technique described here.

Since the ANS senses a wide variety of cardiorespiratory variables, a range of suitable choices are available for use as the input signal. In the example described below, for instance, we employ instantaneous lung volume as the input signal and impose broad-band perturbations on respiratory activity. Other convenient choices for the input variable are discussed in the section on generalization of the method.

As noted above, in order to afford a complete characterization of the ANS from data acquired during a single six-minute test trial, the waveform imposed on the input signal must contain components at all frequencies of interest simultaneously. Any sufficiently broad-band waveform will serve to excite the ANS with multiple simultaneous frequency components. The choice of a particular waveform is made on the basis of what is conveniently realizable for imposition on the input variable used, and what is most suited to the analysis technique employed for determination of the transfer relation between input and output signals. In the example section, we describe one type of broad-band waveform that is particularly easy to impose on the instantaneous lung volume signal.

Once input and output signals have been recorded during the test period of broad-band excitation, any of a wide variety of signal processing techniques may be utilized to compute the transfer relation between the signals. These include both time and frequency domain approaches, and within either category are techniques that make various a priori assumptions about the system behavior. The choice of which signal processing method to use depends on what attribute of the system's behavior is to be probed. In the example presented below, we use a frequency domain approach that yields transfer function magnitude and phase plots derived from the cross-spectrum of the input and output signals.

EXAMPLE

In this example we demonstrate the utility of our technique by showing how it can be used to characterize the behavior of components of the ANS involved in mediation of heart rate fluctuations resulting from respiratory activity. Both sympathetic and parasympathetic divisions of the ANS contribute to this behavior. Since many of the components involved in this control path (e.g., many of the brainstem centers, the heart's pacemaker, and the neural pathways through which the ANS effects changes in cardiovascular function) are also involved in other hemodynamic reflex arcs, the transfer relations found in this example have broad implications regarding general ANS behavior.

The input signal we used, which we denote x(t), was the instantaneous lung volume, measured using a noninvasive volumetric transducer (Respitrace). The output signal y(t) was instantaneous heart rate, derived from the electrocardiogram (ECG) using an event tachometer algorithm. We characterize the response characteristics of the ANS with a complex transfer function $$H(f) = \frac{S_{xy}(f)}{S_{xx}(f)} \quad (1)$$

where $S_{xx}(f)$ is the power spectrum of x(t) and $S_{xy}(f)$ is the cross-spectrum between x(t) and y(t). The complex transfer function H(f) is then decomposed into magnitude and phase components, $|H(f)|$ and $\theta(f)$ respectively, from the real part $H_R(f)$ and the imaginary part $H_I(f)$ of the complex transfer function as follows:

$$|H(f)| = [(H_R(f))^2 + (H_I(f))^2]^{\frac{1}{2}} \quad (2a)$$

$$\theta(f) = \tan^{-1}\frac{H_I(f)}{H_R(f)} \quad (2b)$$

The transfer function magnitude $|H(f)|$ reflects the degree to which input signal content at a frequency f becomes manifest in output signal content at the same frequency. The phase $\theta(f)$ indicates what fraction of the period corresponding to the frequency f the output signal is delayed with respect to the input. This particular representation of the transfer characteristics is useful because it facilitates the development of equivalent electrical circuits to model the system behavior.

As discussed above, the choice of respiratory activity as the input signal to the ANS is not unique; other variables may be chosen which can similarly be measured and perturbed so as to provide the necessary input excitation. Respiration is particularly useful as the input signal since in addition to being easily and noninvasively controllable, it is known to influence autonomic activity through several physiologic mechanisms. First, the cycle of inspiration followed by expiration causes fluctuations in intrathoracic pressure which modulates arterial pressure both directly and through modulation of cardiac filling. Arterial pressure fluctuations are then sensed by the ANS via carotid and aortic baroreceptors. Second, during inspiration, stretch receptors in the chest wall are activated and send signals to the brainstem which affect ANS activity. Third, and perhaps most important, there is likely a direct neural link between the respiratory control center in the brainstem and other ANS centers such as those that control heart rate.

An important aspect of the implementation of our technique in this example is the way in which the perturbing signal, in this case the instantaneous lung volume, is made broad-band without significantly altering the normal respiratory mechanics. In particular, our method preserves the subject's normal residual (postexpiratory) lung volume and allows him to titrate the depth of his inspirations so as to maintain normal blood gases. He is instructed to initiate an inspiratory/expiratory cycle each time he is cued by an audible tone. The tones are generated by a computer, programmed to space the tones evenly in time at some preset rate for a few minutes so that the subject can find a comfortable depth of inspiration. The program then changes modes so that the tones occur with irregular intervals for the next six minutes, but at the same mean rate as during the constant interval sequence. The program can be easily modified to use any desired distribution of intervals between successive tones. Of course, cues other than audible cues may be used. An example is visible cues.

The resulting instantaneous lung volume signal x(t), as measured by impedance plethysmography, approximates the result of convolution between a sequence of unevenly spaced delta functions q(t) and the mean single-cycle respiratory waveform r(t). Thus, $$x(t) = q(t) * r(t) \tag{3}$$

where "*" is the convolution operator. This leads to the following relationship in the frequency domain:

$$S_{xx}(f) = S_{qq}(f) \cdot |R(f)|^2 \tag{4}$$

where $S_{xx}(f)$ is the power spectrum of x(t), $S_{qq}(f)$ is the power spectrum of the pulse sequence q(t), and $|R(f)|^2$ is the Fourier transform magnitude squared of the waveform r(t). The input signal x(t) will be sufficiently broad-band if its power spectrum $S_{xx}(f)$ is significantly non-zero for all frequencies f of interest. This requires that both $S_{qq}(f)$ and $|R(f)|^2$ are non-zero over the same frequency range. $|R(f)|^2$ falls to zero beyond some frequency, but is assumed to remain significantly non-zero to at least 0.5 Hz. In any case r(t), and thus $|R(f)|^2$, can not be modified without altering the subject's respiratory mechanics. The shape of $S_{xx}(f)$ thus depends strongly on the nature of $S_{qq}(f)$ within the frequency band of interest, which in turn depends on the distribution of intervals used.

A sensible choice for the distribution of intervals is that of a Poisson process, since the power spectrum of a sequence of Poisson impulses is a constant over all frequencies. The interpulse interval distribution pt(t) in this case is a decaying exponential in t. Thus, $$pt(t) = \lambda e^{-\lambda t} \tag{5}$$

where $\lambda$ is the mean occurrence rate of the tones. The difficulty with this distribution is that not only can arbitrarily short intervals occur, but such intervals are in fact favored to occur. In practice, we find a subject has difficulty initiating a new respiratory cycle if he is in the midst of an inspiratory/expiratory cycle when he hears the next tone, even though we instruct him to attempt to do so. For this reason, we modify the distribution so as to prohibit intervals shorter than some minimum interval $t_{min}$:

$$p_r(t) = \lambda e^{-\lambda(t - t_{min})} \cdot U(t - t_{min}) \tag{6}$$

where $U(\tau)$ equals unity for $\tau > 0$ and zero otherwise.

With little difficulty, this distribution can be further modified to allow for intervals between both a minimum and maximum limit:

$$p_r(t) = \lambda' e^{-\lambda(t - t_{min})} \cdot U(t - t_{min}) \cdot U(t_{max} - t) \tag{7}$$

$\lambda'$ is a constant greater than $\lambda$ such that $$\int_{t_{min}}^{t_{max}} p_r(t) dt = 1 \tag{8}$$

We find that the imposition of such limits on the intervals greatly improves the ability of the subject to follow the desired breath generating sequence, while only slightly compromising the broad-band nature of the impulse train q(t). It is important to note that even if the power density of the respiratory signal is not constant, the ability to compute an accurate transfer function H(f) is not diminished since variations in $S_{xx}(f)$ will be compensated for when the quotient indicated in equation 1 is computed. However, confidence limits on the value computed for H(f) are expected to be wider in regions along the frequency axis where the input signal power density falls appreciably. The ordinary coherence function $\gamma^2 xy(f)$, computed from the input signal spectrum $S_{xx}(f)$, the output spectrum $S_{yy}(f)$, and the cross-spectrum $S_{xy}(f)$ as follows:

$$\gamma^2_{xy}(f) = \frac{|S_{xy}(f)|^2}{S_{xx}(f) S_{yy}(f)} \tag{9}$$

may be used to provide a quantitative assessment of the confidence, as a function of frequency, of the value computed for H(f) at each frequency. The important issue is that $S_{xx}(f)$ maintain a significantly non-zero level throughout the frequency band of interest, even if the level is not constant.

FIG. 1a shows the power spectrum of the respiratory signal measured for one subject. The distribution of intervals used was $p_r(t)$ of equation 7 with $t_{min} = 1$ sec, $t_{max} = 15$ sec, and mean interval length of 5 sec. Note that while the power density varies considerably over the frequency band from 0.0 to 0.5 Hz, there is nonetheless at least some power at all frequencies.

The technique described above may be used to assess shifts in the relative balance between sympathetic and parasympathetic activity in the mediation of respiratory induced fluctuations in heart rate, from one point in time to another. This is illustrated in the accompanying figures. The respiratory and heart rate power spectra shown in FIGS. 1a and 1b respectively were computed from signals recorded while the subject was standing upright during the six-minute test period. Note that the heart rate signal contains almost no power beyond 0.2 Hz, despite the presence of power in the input excitation throughout the frequency band displayed.

Figure 1:
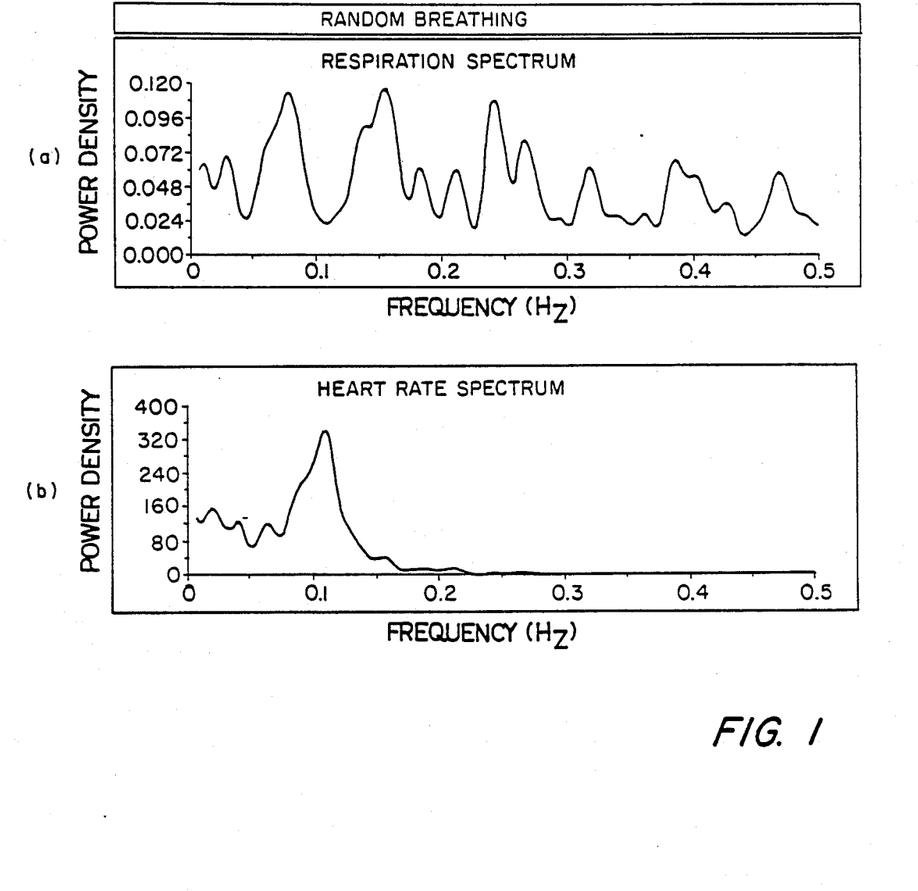
FIG. 1a is a graph of a respiration spectrum.
FIG. 1b is a graph of a heart rate spectrum.
Figure 2:
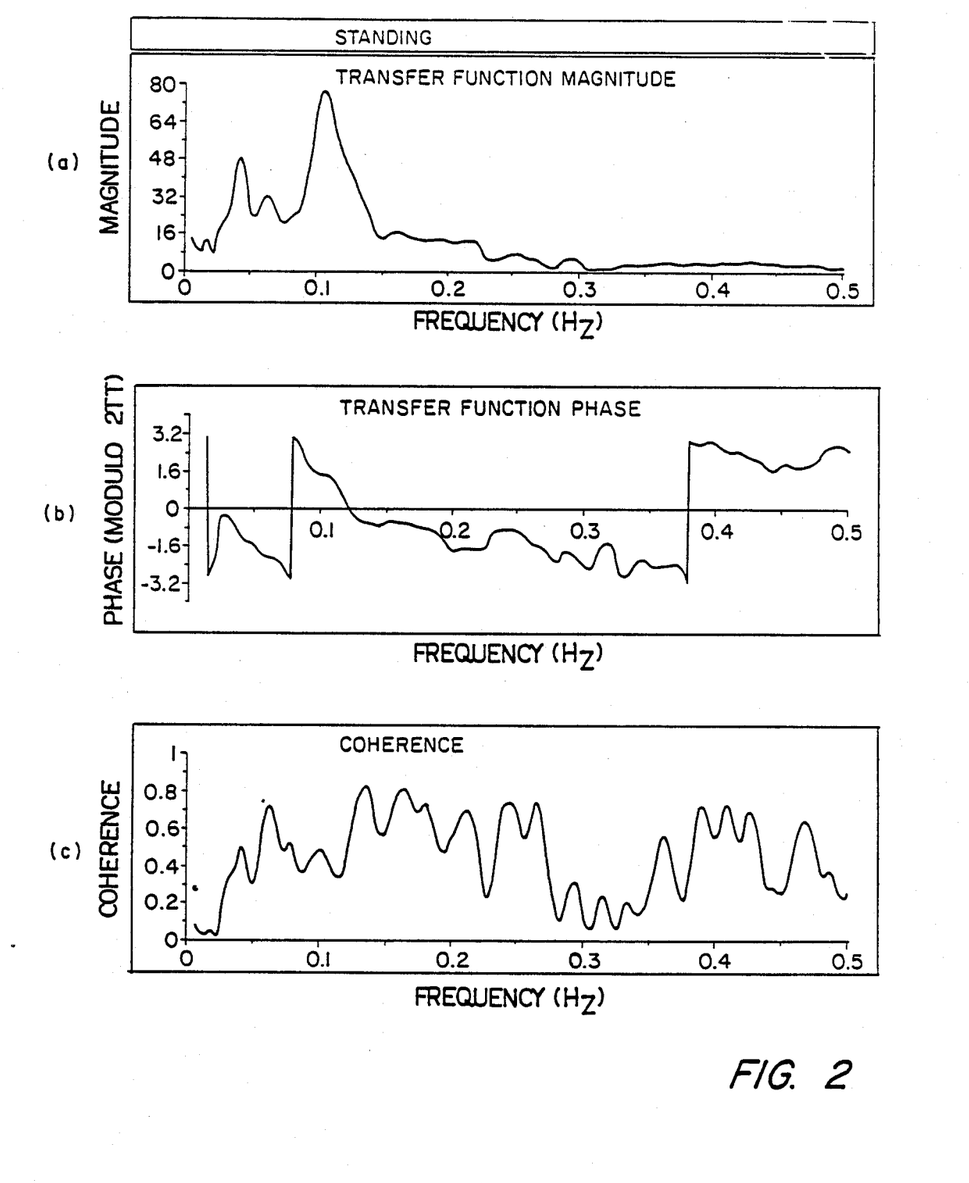
FIG. 2a is a graph of the transfer function magnitude of the data in FIGS. 1a and 1b.
FIG. 2b is a graph of the transfer function phase of the data of FIGS. 1a and 1b.
FIG. 2c is a graph of the coherence computed from the data of FIGS. 2a and 2b.

FIGS. 2a and 2b show the transfer function magnitude and phase plots, where the respiratory and heart rate signals of FIG. 1 are taken to be the input and output signals respectively. The magnitude plot (FIG. 2a) demonstrates the presence of accentuated response regions within the frequency band displayed, most notably around 0.1 Hz. Then from 0.15 Hz to 0.30 Hz, the response magnitude falls gradually, much like a low-order low-pass filter. The phase plot (FIG. 2b) shows roughly linear phase behavior in the region from 0.02 Hz to at least 0.20 Hz, suggesting the presence of a delay element in the control path involved in regulating heart rate. (The phase is plotted modulo $2\pi$, so one must visually "unwrap" the plot to appreciate the linear decline in phase as a function of frequency.) That the autonomic control system regulating heart rate behaves as a low pass filter with a delay is highly suggestive of a predominance of sympathetic activity in the control process. FIG. 2c shows the ordinary coherence function computed from these data. A coherence value of unity at a particular frequency would imply perfectly linear operation of the control network and an absence of corrupting noise in the system. Where the coherence function falls substantially from unity either the system functions less ideally or there exists additive noise that makes the transfer function estimate at those frequencies less reliable. The coherence function thus serves as a check on the transfer function computation.

Figure 3:
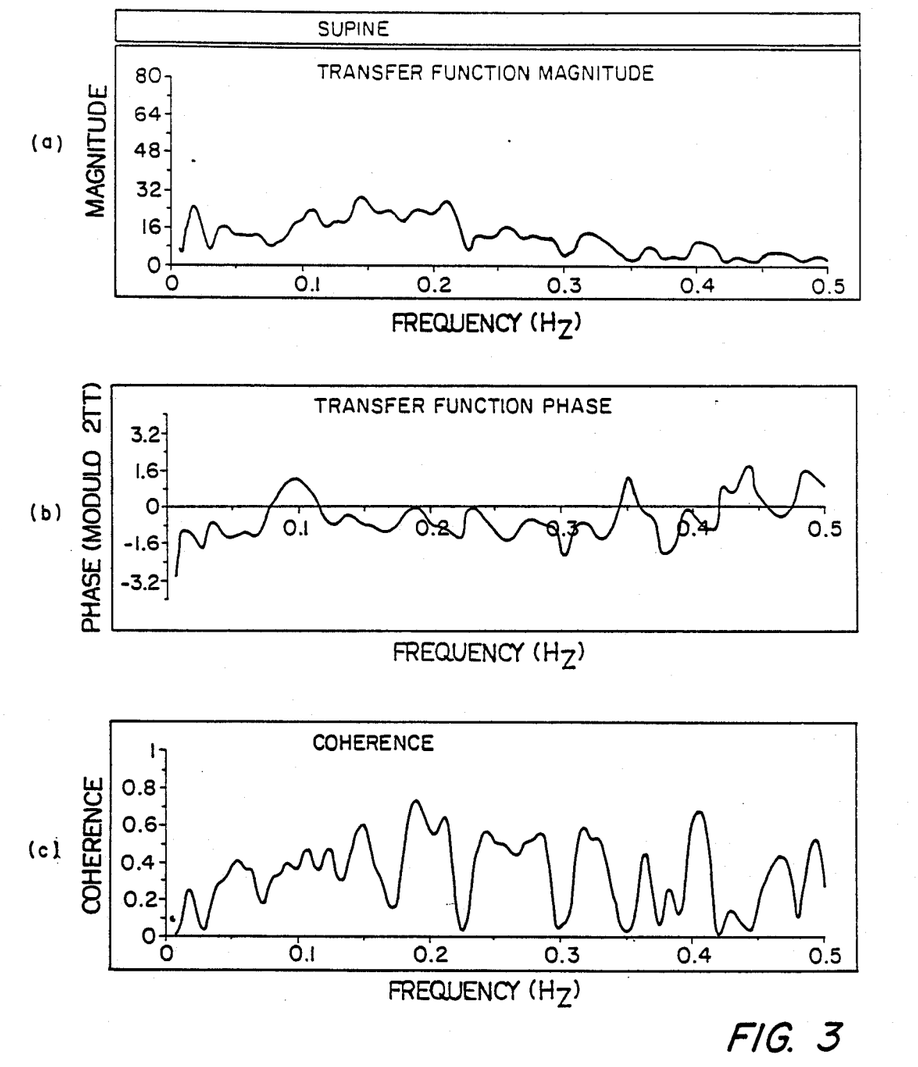
FIGS. 3a, 3b, and 3c are graphs similar to those of FIG. 2 in which the subject is supine.

FIGS. 3a, 3b, and 3c are analogous to FIG. 2a, 2b, and 2c except they were computed from data collected while the subject was supine instead of upright. Note that in contrast to the situation when the subject was upright, the transfer function magnitude in the supine case remains relatively steady over a broad frequency band from 0.02 Hz to at least 0.30 Hz. Also, in this case, the phase plot hovers around zero throughout the frequency band displayed, indicating a lack of any significant delay in the control path. The broad-band responsiveness of the control system without the presence of significant delay in this case suggests parasympathetic activity predominates in the mediation of respiratory-induced heart rate fluctuations when the subject is supine.

This shift in autonomic balance from sympathetic predominance to mostly parasympathetic mediation as the subject lies down from the upright position has been well established by cumbersome and indirect techniques that assess autonomic activity. That our efficient noninvasive method for determination of ANS responsiveness is capable of demonstrating the same result represents a surprising and important new advance in the art of quantifying autonomic function. The changes in autonomic responsiveness demonstrated in this example are in fact quite subtle compared to the dramatic alterations that frequently accompany disease. We therefore expect this approach to be of great utility in patient monitoring for diagnostic purposes and for guiding therapeutic management in both critically ill and ambulatory patients.

Figure 4:
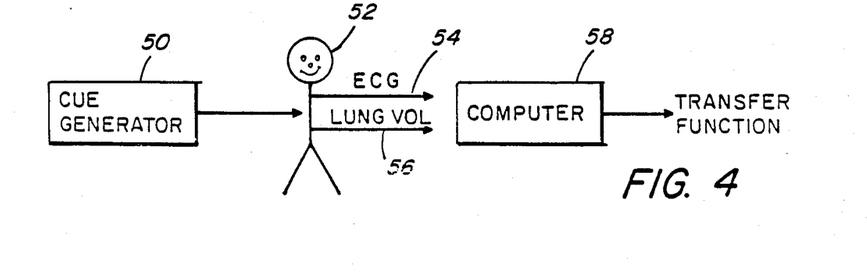
FIG. 4 is a schematic illustration of a hardware implementation of the present invention.

FIG. 4 illustrates a hardware implementation of the above-described methods. A cue generator 50 generates breathing cues and displays them to a human subject 52. The cues from the cue generator 50 may be audible tones or other cues such as visible cues. The cues generated by the cue generator 50 have the broad-band characteristics discussed above. The human subject 52 is instrumented to provide ECG and lung volume signals on lines 54 and 56 as inputs to a computer 58. A suitable computer is a Motorola 68010-based computer system. The computer 58 computes the transfer function as described above. It should be noted that the implementation of FIG. 4 is entirely exemplary, and variables other than the ECG and lung volume may be monitored as inputs to the computer 58 for transfer function analysis. Some other suitable variables will now be described.

The methods outlined in the example above demonstrate how one might characterize autonomic behavior using one particular input signal and one form of transfer analysis. As discussed earlier, there exists a number of hemodynamic variables sensed by the ANS that form suitable choices for input signals. For example, the ANS senses fluctuations in blood pressure in the systemic arterial tree, the pulmonary vasculature, and the cardiac atria. Arterial pressure, particularly in the systemic periphery, is easily measured either minimally invasively via a fluid-filled catheter or noninvasively using a plethysmographic method incorporating a finger cuff [18]. One may thus use this pressure signal as the input, provided he has developed a method for imposing a broad-band signal on it. This may be accomplished by modulating the air pressure in a body suit or neck chamber worn by the subject. Other suitable input signals might include visual stimuli, such as light flashes, auditory cues, and the like.

The broad-band waveform employed for imposition on the input signal also need not be the same as in the example section above. Marmarelis and Marmarelis [15] have discussed the statistical properties of several classes of such waveforms, including Gaussian white noise, random switching signals, and pseudorandum binary signals. Each of these types of broad-band waveforms have different applications, and frequently one is more easily imposed on the input variable used than the others. When arterial pressure is the input variable and is modulated by a neck chamber, for instance, the random switching signal is an ideal choice. In this case, the neck chamber is connected to a Y-valve that toggles between two constant pressure sources at random time intervals.

In some applications it may be desirable to modify the input waveform so as to enrich its spectral content in a specific frequency band. If, for example, the coherence function demonstrates the presence of additive noise corrupting the transfer function estimates within a particular band, then enriching the input signal may improve the signal to noise ratio and thus the transfer function estimates in that band. This selective enrichment may be accomplished in a number of ways, such as through the use of filters that accentuate the spectral content in some frequency bands and attenuate it in others. In the example section above, we discussed another method in which the input signal spectrum could be altered by modifying the distribution of intervals between random events.

Finally, we must emphasize that the signal processing technique utilized in the example section above, namely computation of the transfer function magnitude and phase as a function of frequency, is by no means the only such technique available. It is a particularly useful method when no a priori knowledge about the system under study is available. When a specific model or class of models is known to well describe the behavior of the system, then another signal processing algorithm may provide a more efficient means of characterizing the system than transfer function analysis. Regression techniques, for instance, provide a useful time domain approach for quantifying system behavior when one can assume a maximum time lag over which the value of the input signal at one point in time continues to affect the output.

Each of the fundamental components of our method for analysis of the ANS thus consists of a range of available options. These include a wide variety of choices for the input variable, various broad-band waveforms for use as the input excitation, and a diverse armamentarium of signal processing techniques. One may thus tailor the generalized approach as needed depending on what aspect of autonomic behavior is being probed.

APPENDIX A

1. S. Akselrod, D. Gordon, F. A. Ubel, D. C. Shannon, A. C. Barger, and R. J. Cohen, "Power Spectrum Analysis of Heart Rate Fluctuations: A Quantitative Probe of Beat-to-Beat Cardiovascular Control", *Science*, Vol. 213, pp. 220–222 (1981).
2. S. Akselrod, D. Gordon, J. B. Madwed, N. C. Snidman, D. C. Shannon, and R. J. Cohen, "Hemodynamic Regulation: Investigation by Spectral Analysis", *Am. J. Physiol.*, (in press).
3. G. F. Chess and F. R. Calaresu, "Frequency Response Model of Vagal Control of Heart Rate in the Cat", *Am. J. Physiol.*, Vol. 220, pp. 554–557 (1971).
4. G. F. Chess, R. M. K. Tam, and F. R. Calaresu, "Influence of Cardiac Neural Inputs on Rhythmic Variations of Heart Period in the Cat", *Am. J. Physiol.*, Vol. 228, pp. 775–780 (1975).
5. R. W. DeBoer, J. M. Karemaker, and J. Strackee, "Comparing Spectra of a Series of Point Events Particularly for Heart Rate Variability Data", *IEEE Trans. Biomed. Eng.*, Vol. BME-31, pp. 384–387 (1984).
6. R. W. DeBoer, J. M. Karemaker, and J. Strackee, "Beat-to-Beat Variability of Heart Interval and Blood Pressure", *Automedica*, Vol. 4, pp. 217–222 (1983).
7. R. W. DeBoer, J. M. Karemaker, and J. Strackee, "Relationship Between Short-term Blood-pressure Fluctuations and Heart-rate variability in Resting Subjects I: A Spectral Analysis Approach", *Med.-+Biol. Eng.+Comp.*, Vol. 23, (1985).
8. G. N. Franz, A. M. Scher, and C. S. Ito, "Small Signal Characteristics of Carotid Sinus Baroreceptors of Rabbits", *J. Applied Physiol.*, Vol. 30, pp. 527–535 (1971).
9. B. W. Hyndman and J. R. Gregory, "Spectral Analysis of Sinus Arrhythmia During Mental Loading", *Ergonomics*, Vol. 18, pp. 255–270 (1975).
10. R. I. Kitney, T. Fulton, A. H. McDonald, and D. A. Linkens, "Transient Interactions Between Blood Pressure, Respiration and Heart Rate in Man", *in press*, ().
11. C. F. Knapp, J. M. Evans, D. C. Randall, and J. A. Marquis, "Cardiovascular Regulation in Canines During Low-frequency Acceleration", *Am. J. Physiol.*, Vol. 243, pp. H998–H1009 (1982).
12. W. H. Levison, G. O. Barnett, and W. D. Jackson, "Nonlinear Analysis of the Baroreceptor Reflex System", *Circ. Res.*, Vol. 18, pp. 673–682 (1966).
13. T. C. Lloyd, "Cardiopulmonary Baroreflexes: Integrated Responses to Sine- and Square-wave Forcing", *J. Applied Physiol.*, Vol. 35, pp. 870–874 (1973).
14. H. Luczak and W. Laurig, "An Analysis of Heart Rate Variability", *Ergonomics*, Vol. 16, pp. 85–97 (1973).
15. P. Z. Marmarelis and V. Z. Marmarelis, "Analysis of Physiological Systems", Plenum Press, New York (1978).
16. J. Penaz, N. Honzikova, and B. Fizer, "Spectral Analysis of Resting Variability of Some Circulatory Parameters in Man", *Physiol. Bohem.*, Vol. 27, pp. 349–357 (1978).
17. J. Penaz, "Frequency Response of the Cardiac Chronotropic Action of the Vagus in the Rabbit", *Arch. Int. Physio. Bioch.*, Vol. 70, pp. 636–650 (1962).
18. J. Penaz, "Photoelectric Measurement of Blood Pressure, Volume and Flow in the Finger", *Digest 10th Int'l. Conf. Med. Bio. Eng.*, p. 104 (1973).
19. B. Pomeranz, R. J. B. McCaulay, M. A. Caudill, I. Kutz, D. Adam, D. Gordon, K. M. Kilborn, A. C. Barger, D. C. Shannon, R. J. Cohen, and H. Benson, "Assessment of Autonomic Function in Humans by Heart Rate Spectral Analysis", *Am. J. Physiol.*, Vol. 248, pp. H151–H153 (1985).
20. A. M. Scher, W. W. Ohm, K. Bumgarner, R. Boynton, and A. C. Young, "Sympathetic and Parasympathetic Control of Heart Rate in the Dog, Baboon and Man", *Fed. Proc.*, Vol. 31, pp. 1219–1225 (1972).
21. A. M. Scher and A. C. Young, "Servoanalysis of Carotid Sinus Reflex Effects on Peripheral Resistance", *Cir. Res.*, Vol. 12, pp. 152–162 (1963).
22. A. M. Scher and A. C. Young, "Reflex Control of Heart Rate in the Unanesthetized Dog", *Am. J. Physiol.*, Vol. 218, pp. 780–789 (1970).
23. J. W. Spickler, P. Kezdi, and E. Geller, "Transfer Characteristics of the Carotid Sinus Pressure Control System", pp. 31–40 in *Baroreceptors and Hypertension*, ed. P. Kezdi, Pergamon Press, Oxford (1967).
24. M. G. Taylor, "Use of Random Excitation and Spectral Analysis in the Study of Frequency-dependent Parameters of the Cardiovascular System", *Circ. Res.*, Vol. 18, pp. 585–595 (1966).
25. U. Zwiener, "Physiological Interpretation of Autospectra, Coherence and Phase Spectra of Blood Pressure, Heart Rate, and Respiration Waves in Man", *Automedica*, Vol. 2, pp. 161–169 (1978).

We claim:

1. Method for assessing autonomic response comprising:
    applying a broad-band perturbation to a physiologic input signal sensed by the autonomic nervous system;
    monitoring a physiologic output signal modulated by the autonomic nervous system;
    computing the transfer relation between the physiologic input and output signals; and displaying said transfer relation.

2. The method of claim 1 wherein the input signal to which the broad-band perturbation is applied is respiratory activity.

3. The method of claim 1 wherein the physiologic output signal is heart rate.

4. The method of claim 1 in which the broad-band perturbation has a Poisson distribution.

5. The method of claim 1 wherein the broad-band perturbation has a Poisson distribution modified to prohibit intervals shorter than some minimum interval $t_{min}$.

6. The method of claim 1 wherein the broad-band perturbation is a Poisson distribution modified to prohibit intervals shorter than some minimum interval $t_{min}$ or longer than some maximum interval $t_{max}$.

7. The method of claim 1 wherein the broad-band perturbation lasts for approximately 6 minutes.

8. The method of claim 1 wherein the broad-band perturbation contains components in the range of 0.0–0.5 Hz.

9. The method of claim 1 wherein the transfer relation is a complex transfer function.

10. The method of claim 1 wherein the autonomic response is assessed on a standing subject.

11. The method of claim 1 wherein the autonomic response is assessed on a supine subject.

12. The method of claim 1 wherein the broad-band perturbation is applied to arterial pressure as the input signal.

13. The method of claim 1 wherein the broad-band perturbation has a Gaussian white noise distribution.

14. The method of claim 1 wherein the broad-band perturbation has a random switching signal distribution.

15. The method of claim 1 wherein the broad-band perturbation has a pseudo random binary distribution.

16. The method of claim 1 wherein the broad-band perturbation is modified in a specific frequency band.

17. The method of claim 1 wherein the physiologic output signal is a hemodynamic parameter.

18. The method of claim 1 wherein the perturbation is auditory stimuli.

19. The method of claim 1 wherein the perturbation is visual stimuli.

20. The method of claim 19 wherein the visual stimuli are light flashes.

21. The method of claim 9 wherein the complex transfer function is decomposed into magnitude and phase components.

22. The method of claim 12 wherein arterial pressure variations are accomplished by modulating air pressure in a body suit or neck chamber worn by a subject.

23. Method for assessing autonomic response comprising:
    applying a broad-band perturbation to respiratory activity which is the input signal sensed by the autonomic nervous system;
    monitoring heart rate as the output signal modulated by the autonomic nervous system;
    computing the transfer relation between respiratory activity and heart rate; and displaying said transfer relation.

24. Method for assessing autonomic response comprising:
    applying a broad-band perturbation to a physiologic parameter which is the input signal sensed by the autonomic nervous system;
    monitoring an output signal which is a physiologic parameter which is modulated by the autonomic nervous system
    characterizing the relationship between the input and output signals; and displaying said transfer relation.

25. The method of claim 24 wherein the relationship between the input signal and the output signal is performed by a regression analysis.

26. Apparatus for assessing autonomic response comprising:
    means for subjecting a physiologic parameter sensed by the autonomic system as an input signal to a broad-band perturbation;
    means for monitoring an output signal which is a physiologic parameter modulated by the autonomic nervous system; and
    means for computing the relationship between the input and output signals; and means for displaying said transfer relation.

27. The apparatus of claim 26 wherein the broad-band perturbation is applied to respiratory activity as the input 28. The apparatus of claim 26 wherein the physiologic is heart rate.

29. The apparatus of claim 26 wherein the relationship between the input signal and the output signal is a transfer function.

30. The apparatus of claim 26 wherein the broad-band perturbation applied to respiratory activity as the input signal is induced by external cues to which the subject is trained to respond.

31. The apparatus of claim 26 wherein the broad-band perturbation has a Poisson distribution.

32. The apparatus of claim 26 wherein the relationship between the input signal and the output signal is determined by a regression analysis.

33. The apparatus of claim 26 wherein the output signal is a hemodynamic parameter.

* * * * *

UNITED STATES PATENT AND TRADEMARK OFFICE
CERTIFICATE OF CORRECTION

PATENT NO. : 4,777,960
DATED : October 18, 1988
INVENTOR(S) : Ronald D. Berger et al.

It is certified that error appears in the above-identified patent and that said Letters Patent are hereby corrected as shown below:

Column 12, line 6, delete "and".

Column 12, line 12, after "input", insert --signal.--.

Column 12, line 14, after "logic", insert --output signal--.

Signed and Sealed this

Twenty-eighth Day of March, 1989

Attest:

DONALD J. QUIGG

*Attesting Officer*  *Commissioner of Patents and Trademarks*